United States Patent
Brown et al.

(10) Patent No.: US 12,290,625 B2
(45) Date of Patent: May 6, 2025

(54) COLLAPSIBLE MOBILE URINE CONTAINER

(71) Applicant: Art Brown, Eighty-Four, PA (US)

(72) Inventors: Art Brown, Eighty-Four, PA (US); Jonathan Weir, Venetia, PA (US); Michael Laskowski, Pittsburgh, PA (US); Hyukjae Chang, Pittsburgh, PA (US)

(73) Assignee: Art Brown, Eighty-Four, PA (US)

( * ) Notice: Subject to any disclaimer, the term of this patent is extended or adjusted under 35 U.S.C. 154(b) by 0 days.

(21) Appl. No.: 18/435,786

(22) Filed: Feb. 7, 2024

(65) Prior Publication Data

US 2024/0261489 A1     Aug. 8, 2024

Related U.S. Application Data

(60) Provisional application No. 63/444,132, filed on Feb. 8, 2023, provisional application No. 63/607,441, filed on Dec. 7, 2023.

(51) Int. Cl.
*A61M 1/00*     (2006.01)

(52) U.S. Cl.
CPC ..................... *A61M 1/69* (2021.05)

(58) Field of Classification Search
CPC .. A61F 5/455; A61F 5/451; A61F 5/44; A61F 5/453; A61G 9/00; B67C 11/00; B65D 21/02; B65D 1/06; B65D 1/40; B65D 21/00; B65D 21/08; B65D 43/02; B65D 6/18; B65D 8/14; B65D 1/0292; B65D 5/40; A61M 39/08; A47K 11/12
See application file for complete search history.

(56) References Cited

U.S. PATENT DOCUMENTS

| | | | | |
|---|---|---|---|---|
| 1,663,966 A | * | 3/1928 | Ament | A47K 11/06 220/9.3 |
| 3,602,924 A | * | 9/1971 | Kneisley | A47B 45/00 4/315 |
| 3,721,243 A | * | 3/1973 | Hesterman | A61F 5/453 604/245 |
| 4,233,263 A | | 11/1980 | Schaeffer | |
| 4,492,258 A | | 1/1985 | Lichtenstein et al. | |

(Continued)

FOREIGN PATENT DOCUMENTS

| | | |
|---|---|---|
| CA | 1112836 A | 11/1981 |
| CA | 1232809 A | 2/1988 |

(Continued)

*Primary Examiner* — Michele Kidwell
(74) *Attorney, Agent, or Firm* — The Webb Law Firm

(57) ABSTRACT

A collapsible mobile urine container includes a container body made of malleable polymeric material having a body wall comprised of a bag or a tube, and a support member being a wire coil. The container further includes a shell having a top, a bottom, and a hinge, and the shell is configured to enclose the container body. The container body is configured to be collapsible such that it is collapsed in a first state and extended in a second state. A method of using a collapsible mobile urine container includes providing a collapsible mobile urine container, opening the container shell, extending the container body to the second state, positioning the container body relative to a user to collect urine, and collecting urine during a urination event.

14 Claims, 18 Drawing Sheets

(56) References Cited

U.S. PATENT DOCUMENTS

| | | | |
|---|---|---|---|
| 4,531,245 A * | 7/1985 | Lowd | A61G 9/006 604/347 |
| 4,603,152 A | 7/1986 | Laurin et al. | |
| 4,700,856 A * | 10/1987 | Campbell | A61J 9/001 215/11.1 |
| 4,979,242 A * | 12/1990 | Maggio | E04H 1/1244 135/901 |
| 5,065,459 A * | 11/1991 | Tjahaja | A61F 5/44 4/144.2 |
| 5,080,149 A | 1/1992 | Peoples | |
| 5,370,637 A * | 12/1994 | Brodeur | A61F 5/4556 4/144.3 |
| 5,384,138 A | 1/1995 | Robbins, III et al. | |
| 5,511,557 A * | 4/1996 | Hazard | A61B 10/007 600/573 |
| 5,632,406 A | 5/1997 | Robbins, III | |
| 6,054,099 A | 4/2000 | Levy | |
| 6,070,275 A | 6/2000 | Garlock | |
| 6,191,192 B1 | 2/2001 | Monden et al. | |
| 6,199,220 B1 * | 3/2001 | Smith | A47K 11/045 4/144.2 |
| 6,202,224 B1 * | 3/2001 | Freeman | A47K 11/00 4/144.1 |
| 6,363,541 B1 * | 4/2002 | Tylka | A47K 11/06 4/144.1 |
| 6,455,610 B1 | 9/2002 | Lever et al. | |
| 6,662,964 B2 | 12/2003 | Higuchi | |
| 6,668,388 B2 * | 12/2003 | Buttigieg | A61G 9/006 4/144.2 |
| 6,702,143 B2 * | 3/2004 | Wang | B65D 1/32 220/666 |
| 6,840,164 B2 | 1/2005 | Eastman | |
| 8,133,423 B2 | 3/2012 | Tang et al. | |
| 8,192,412 B2 | 6/2012 | Waller | |
| 8,235,956 B2 | 8/2012 | Block | |
| 8,511,895 B2 * | 8/2013 | Burchfield | B65F 1/1415 383/33 |
| 8,852,171 B2 * | 10/2014 | Lund | A61M 25/002 604/327 |
| 9,826,866 B2 | 11/2017 | Kuo | |
| 10,196,169 B2 | 2/2019 | Tsui | |
| 10,517,377 B2 | 12/2019 | Lyon et al. | |
| 11,465,797 B2 | 10/2022 | Swarts et al. | |
| 2002/0066735 A1 * | 6/2002 | Hewlitt | B65D 77/06 220/495.06 |
| 2005/0175748 A1 | 8/2005 | Thijssen et al. | |
| 2007/0061951 A1 * | 3/2007 | Snider | A47K 11/12 4/144.2 |
| 2009/0215924 A1 | 8/2009 | Zhu et al. | |
| 2010/0136073 A1 | 6/2010 | Preuss et al. | |
| 2012/0210503 A1 | 8/2012 | Anzivino, Sr. et al. | |
| 2014/0207112 A1 | 7/2014 | Hale | |
| 2015/0175336 A1 | 6/2015 | Morris et al. | |
| 2016/0130026 A1 * | 5/2016 | Brown | B65D 1/40 215/228 |
| 2017/0281824 A1 | 10/2017 | Ryan et al. | |
| 2017/0303539 A1 | 10/2017 | Fliss et al. | |
| 2020/0138620 A1 * | 5/2020 | Schwab | A61F 5/453 |
| 2022/0312944 A1 * | 10/2022 | Tourpouzidis | B65D 83/0077 |

FOREIGN PATENT DOCUMENTS

| | | | | |
|---|---|---|---|---|
| CN | 2252781 Y | * | 4/1997 | B65D 37/00 |
| EP | 0184629 A2 | | 6/1986 | |
| EP | 0 138 427 | * | 3/1990 | A61L 15/00 |
| EP | 0887373 A2 | | 12/1998 | |
| GB | 2331501 | * | 5/1999 | B65D 1/00 |
| GB | 2388358 | * | 11/2003 | B65D 1/02 |
| GB | 2575055 | * | 1/2020 | A61F 5/453 |
| WO | 2020/097399 | * | 5/2020 | A61F 5/451 |

* cited by examiner

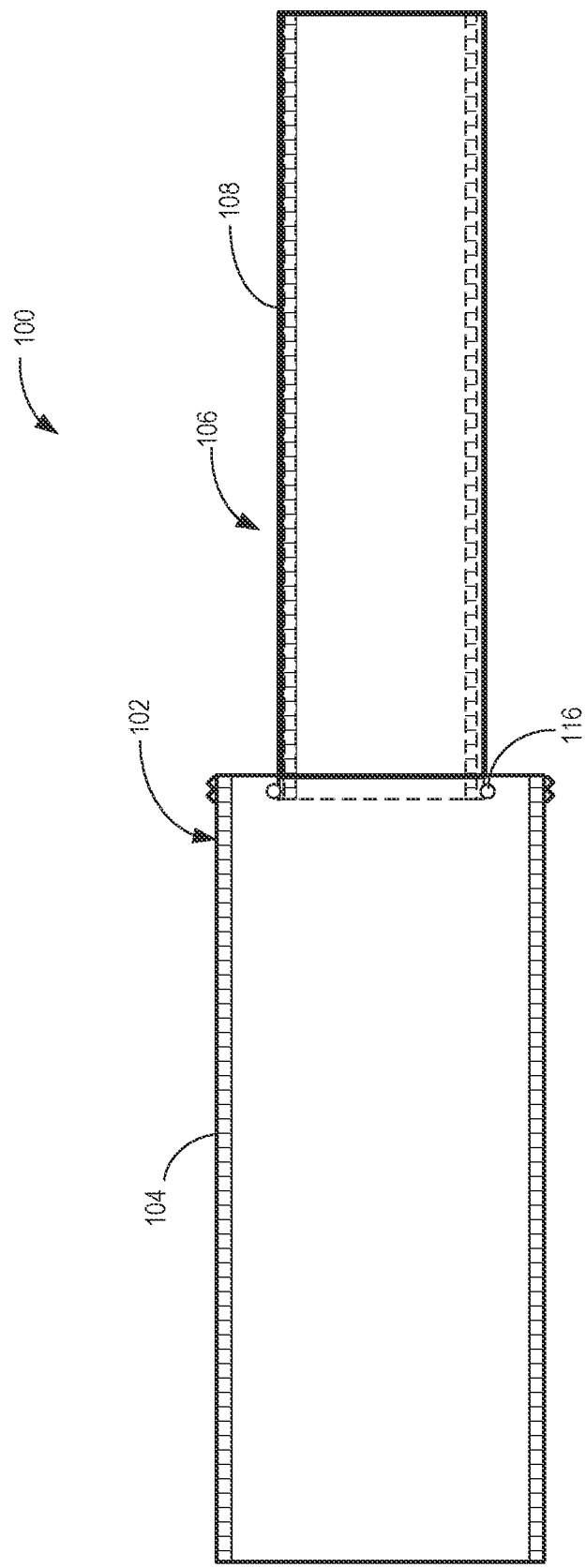

COLLAPSIBLE MOBILE URINE CONTAINER

CROSS-REFERENCE TO RELATED APPLICATIONS

This application claims the benefit of U.S. Provisional Patent Application No. 63/444,132, which was filed Feb. 8, 2023, and of U.S. Provisional Patent Application No. 63/607,441 which was filed Dec. 7, 2023, the disclosures of which are hereby incorporated by reference in their entirety.

BACKGROUND

Field of the Disclosure

The present disclosure relates to a collapsible mobile urine container for mobile urine collection, discrete use, sterility, and disposability.

Description of Related Art

Certain medical disorders, including benign prostatic hyperplasia (BPH), also known as prostate gland enlargement, are common conditions in aging individuals and are especially common in men over 55 years of age. The enlargement makes urination for these individuals frequent, and in some cases, a painful emergency. Additionally, men and women with urinary or kidney tract infections may suffer from frequent or uncontrollable urinations. BPH can sometimes lead to the development of such infections. The human bladder has a valve in the urinary tract. This valve can be over pressurized resulting in symptoms including pain and uncontrollable urination. This results in situations where urination must occur immediately despite circumstances such as being in a moving vehicle or stuck in traffic, and can potentially result in urinating while fully dressed. Other possible results of prolonged urinary relief where circumstances do not allow for relief of a bladder include the potential for damage to the valve and further development of infections. However, immediate urination in certain instances is often inconvenient, if not impossible.

A variety of solutions exist to allow for urinating in an environment where a toilet or restroom facility is not available. These solutions include the use of empty drink bottles or jugs, or other containers specifically designed for urine containment. However, common drink bottles are inadequate and unsanitary, and currently available containers for urination events in situations as described above are often cumbersome, difficult to use, and do not adequately contain the liquid. Additionally, emergency urination events can be embarrassing for those who suffer from them, and that embarrassment may be amplified by the need to carry a urine container. Further, available containers are often unsafe due to their lack of sterility, and thus, their potential to cause infection or illness.

In view of the foregoing, there exists a need for a collapsible mobile urine container for urine collection, discrete use, sterility, and disposability.

SUMMARY

Accordingly, aspects of the present disclosure are directed to non-limiting embodiments of a collapsible mobile urine container.

According to an aspect of the disclosure, a collapsible mobile urine container may include a container body made of malleable polymeric material and may have a body wall, a top, and a bottom, and the container body may be configured to be collapsible.

According to another aspect of the disclosure, a collapsible mobile urine container may include a container body comprised of malleable polymeric material and having a body wall, a support member, and a container shell. The container body may be configured to be collapsible such that it may be collapsed in a first state and extended in a second state. The container shell may be configured to enclose the container body in the first state.

According to another aspect of the disclosure, a method of using a collapsible mobile urine container may include providing a collapsible mobile urine container, which may include a container body comprised of malleable polymeric material and having a body wall, a support member, and a container shell. The container body may be configured to be collapsible such that it may be collapsed in a first state and extended in a second state. The container shell may be configured to enclose the container body in the first state. The method may further include opening the container shell, extending the container body to the second state, positioning the container body relative to a user to collect urine, and collecting urine during a urination event.

Non-limiting illustrative examples of embodiments of the present disclosure will now be described in the following numbered clauses.

Clause 1: A collapsible mobile urine container, comprising: a container body comprised of malleable polymeric material and having a body wall, a top, and a bottom, wherein the container body is configured to be collapsible.

Clause 2: The collapsible mobile urine container of clause 1, wherein the top comprises a cap.

Clause 3: The collapsible mobile urine container of clauses 1 or 2, wherein the bottom comprises a cover and the cover comprises a tab.

Clause 4: The collapsible mobile urine container of any of clauses 1-3, wherein the top further comprises gripping members, a hinge, and a tab.

Clause 5: The collapsible mobile urine container of any of clauses 1-4, wherein the container body is configured to be collapsible such that it is compact or small enough to fit in a glove box of a vehicle, a clothes pocket, a purse, a bag, or the like.

Clause 6: The collapsible mobile urine container of any of clauses 1-5, wherein the body wall is a bag or a tube.

Clause 7: The collapsible mobile urine container of any of clauses 1-6, wherein the container body further comprises a support member, and the support member is a coil.

Clause 8: The collapsible mobile urine container of any of clauses 1-7, wherein the container has a total thickness of less than one inch in a collapsed first state, wherein the container has a total height of between six and nine inches in an extended second state, and wherein the container has an outer diameter of less than four inches.

Clause 9: The collapsible mobile urine container of any of clauses 1-8, wherein the container further comprises: a flexible tube comprised of malleable polymeric material, having a tube wall, a first end, and a second end; a cap; and packaging comprised of sterile material, wherein the container body is configured to be collapsible; wherein the flexible tube is positioned inside the container body and is configured to be collapsible; and wherein the packaging is configured to enclose the collapsed container body in a first state until use, the container body and flexible tube are configured to be extendible defining a second state, and the flexible tube is further extendible such that the second end of the flexible tube is pulled to the top of the container body and the first end of the flexible tube protrudes from the top of the container body defining a third state.

Clause 10: A collapsible mobile urine container of any of clauses 1-9, comprising: a container body comprised of malleable polymeric material and having a body wall and a support member; and a container shell; wherein the container body is configured to be collapsible such that it is collapsed in a first state and extended in a second state, and wherein the container shell is configured to enclose the container body in the first state.

Clause 11: The collapsible mobile urine container of any of clauses 1-10, wherein the body wall comprises a bag or a tube.

Clause 12. The collapsible mobile urine container of any of clauses 1-11, wherein the support member is a wire coil.

Clause 13: The collapsible mobile urine container of any of clauses 1-12, wherein the wire coil is a flat spring, and wherein the support member is coaxial with the container body and extends from a first end of the container body to a second end of the container body.

Clause 14: The collapsible mobile urine container of any of clauses 1-13, wherein the support member is coaxial with the container body and extends a distance from a first end of the container body such that, in the second state, a height of the support member is less than a height of the container body.

Clause 15: The collapsible mobile urine container of any of clauses 1-14, wherein the support member is coaxial with the container body and extends a distance from a second end of the container body such that, in the second state, a height of the support member is less than a height of the container body.

Clause 16: The collapsible mobile urine container of any of clauses 1-15, wherein the container shell further comprises a top and a bottom, and wherein the top and the bottom are hingedly connected such that an axis of a hinge connecting the top and the bottom is perpendicular to a central axis of the container shell.

Clause 17: The collapsible mobile urine container of any of clauses 1-16, wherein the container shell further comprises a top and a bottom, and wherein the top and the bottom are hingedly connected such that an axis of a hinge connecting the top and the bottom is parallel to a central axis of the container shell.

Clause 18: The collapsible mobile urine container of any of clauses 1-17, wherein the container body is removable from the container shell.

Clause 19: The collapsible mobile urine container of any of clauses 1-18, wherein the container body has a total thickness of less than one inch in a collapsed first state, wherein the container shell has a total thickness of less than one inch in a closed position, wherein the container body has a total height of between six and nine inches in an extended second state, and wherein the container body has an outer diameter of less than four inches.

Clause 20: A method of using a collapsible mobile urine container, the method comprising: providing a collapsible mobile urine container of any of clauses 1-19, the collapsible mobile urine container comprising: a container body comprised of malleable polymeric material and having a body wall and a support member; and a container shell; wherein the container body is configured to be collapsible such that it is collapsed in a first state and extended in a second state, and wherein the container shell encloses the container body in the first state; opening the container shell; extending the container body to the second state; positioning the container body relative to a user to collect urine; and collecting urine during a urination event.

Further details and advantages of the various examples described in detail herein will become clear upon reviewing the following detailed description of the various examples in conjunction with the accompanying drawing figures.

BRIEF DESCRIPTION OF THE DRAWINGS

Additional advantages and details are explained in greater detail below with reference to the exemplary embodiments that are illustrated in the accompanying schematic figures, in which:

FIG. 4 is a side view of a non-limiting embodiment of a collapsible mobile urine container in a third state in accordance with the present disclosure;

Corresponding reference characters indicate corresponding parts throughout the several views. The exemplifications set out herein illustrate exemplary embodiments of the disclosure, and such embodiment are not to be construed as limiting the scope of the disclosure in any manner.

DETAILED DESCRIPTION

Figure 1:
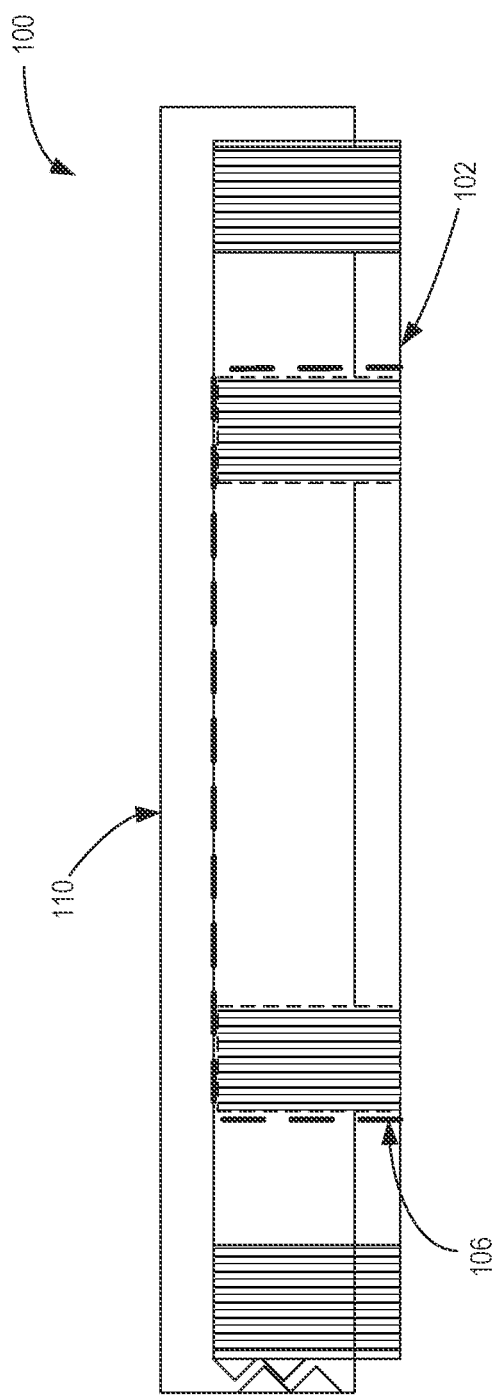
FIG. 1 is a side sectional view of a non-limiting embodiment of a collapsible mobile urine container in a first state in accordance with the present disclosure.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "top," "bottom," and derivatives thereof may relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

Embodiments of the present disclosure are generally directed to a collapsible mobile urine container for mobile urine collection, discrete use, sterility, and disposability.

According to non-limiting embodiments, a collapsible mobile urine container may include a container body made of malleable polymeric material and may have a body wall, a top, and a bottom, and the container body may be configured to be collapsible.

According to other non-limiting embodiments, a collapsible mobile urine container may include a container body comprised of malleable polymeric material and having a body wall, a support member, and a container shell. The container body may be configured to be collapsible such that it may be collapsed in a first state and extended in a second state. The container shell may be configured to enclose the container body in the first state. In some non-limiting embodiments, the body wall may comprise a bag or a tube. In some non-limiting embodiments, the support member may be a wire coil. In some non-limiting embodiments, the wire coil may be a flat spring.

In some non-limiting embodiments, the support member may be coaxial with the container body and may extend from a first end of the container body to a second end of the container body. In some non-limiting embodiments, the support member may be coaxial with the container body and may extend a distance from a first end of the container body such that, in the second state, a height of the support member is less than a height of the container body. In some non-limiting embodiments, the support member may be coaxial with the container body and may extend a distance from a second end of the container body such that, in the second state, a height of the support member is less than a height of the container body.

In some non-limiting embodiments, the container shell may further include a top and a bottom. In some non-limiting embodiments, the top and the bottom may be hingedly connected such that an axis of a hinge connecting the top and the bottom may be perpendicular to a central axis of the container shell. In some non-limiting embodiments, the top and the bottom may be hingedly connected such that an axis of a hinge connecting the top and the bottom may be parallel to a central axis of the container shell.

In some non-limiting embodiments, the container body may be removable from the container shell.

According to other non-limiting embodiments, a method of using a collapsible mobile urine container may include providing a collapsible mobile urine container, which may include a container body comprised of malleable polymeric material and having a body wall, a support member, and a container shell. The container body may be configured to be collapsible such that it may be collapsed in a first state and extended in a second state. The container shell may be configured to enclose the container body in the first state. The method may further include opening the container shell, extending the container body to the second state, positioning the container body relative to a user to collect urine, and collecting urine during a urination event.

In this way, embodiments of the present disclosure allow for a collapsible mobile urine container for mobile urine collection, discrete use, sterility, and disposability.

Referring now to FIG. 1, FIG. 1 is a side view of a non-limiting embodiment of collapsible mobile urine container 100 in a first state. As shown in FIG. 1, container 100 may include container body 102, flexible tube 106, and cap 110. As shown in FIG. 1, container body 102 may be made of a malleable polymeric material and flexible tube 106 may be positioned within container body 102 and may be made of a malleable polymeric material so that collapsible mobile urine container 100 may be collapsed to a minimal and concealable size in a first state, such that container 100 may be easily and discretely stored in a clothes pocket, purse, or bag. In this first state, container body 102 may be collapsed to a height of less than three-eighths (⅜) of an inch to allow for concealment. As further shown in FIG. 1, in a first state of collapsible mobile urine container 100, cap 110 may be in place on container body 102.

Figures 2A, 2B:
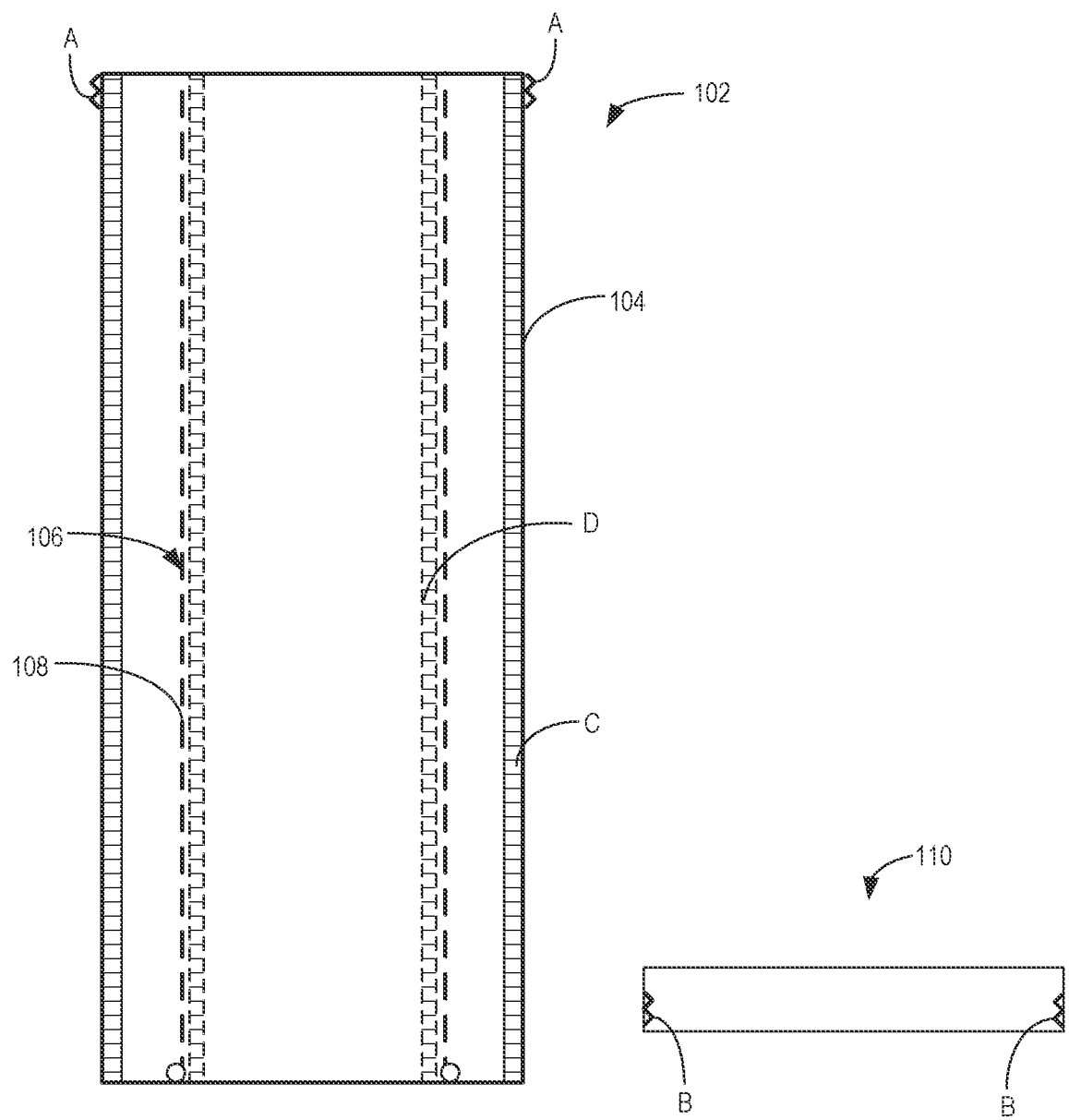
FIGS. 2A and 2B are side views of a non-limiting embodiment of a collapsible mobile urine container in a second state in accordance with the present disclosure.
Figures 3A, 3B:
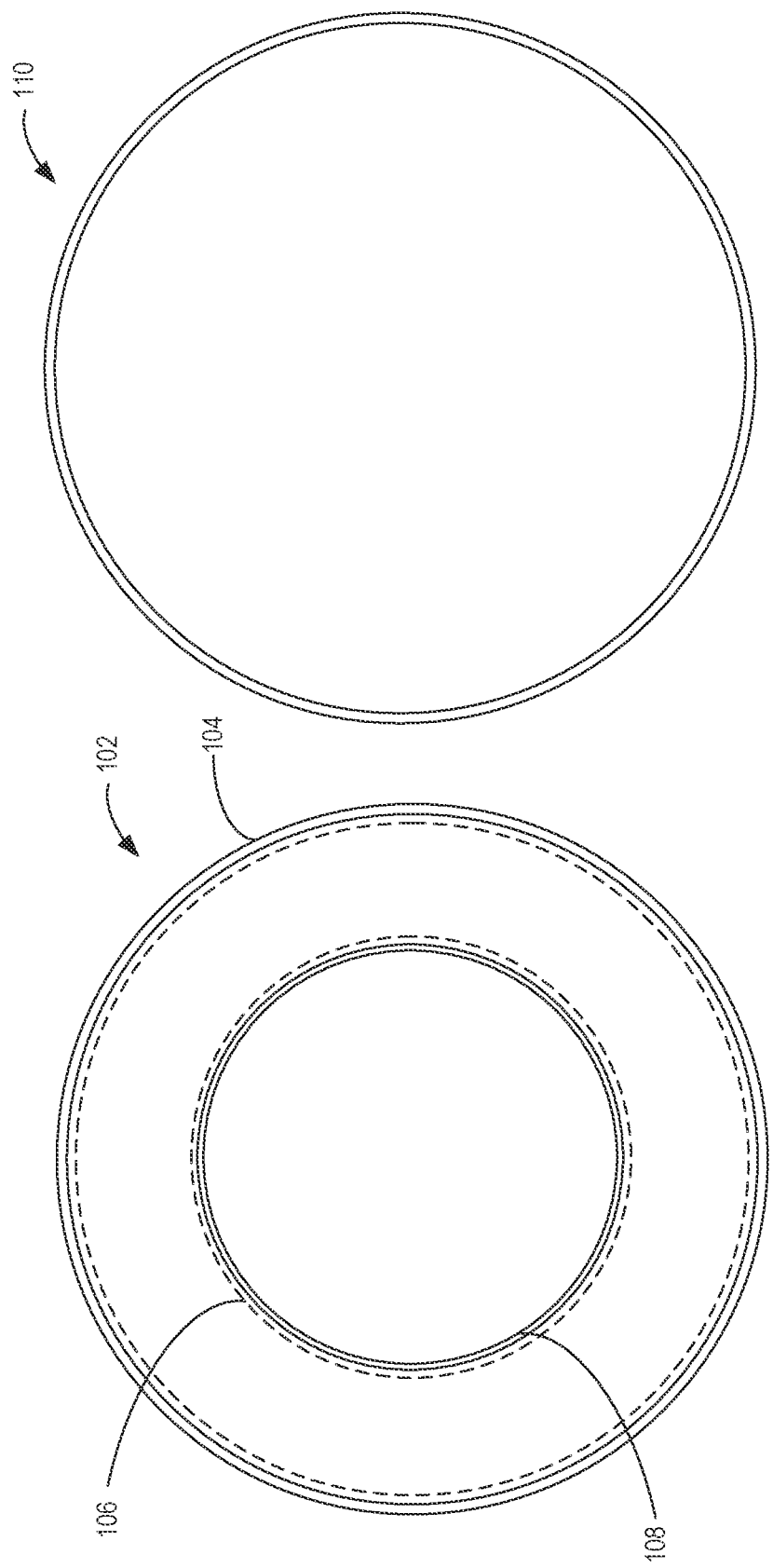
FIGS. 3A and 3B are plan views of a non-limiting embodiment of a collapsible mobile urine container in a second state in accordance with the present disclosure.

Referring now to FIGS. 2A and 2B and FIGS. 3A and 3B, FIGS. 2A and 2B are side views and FIGS. 3A and 3B are plan views of a non-limiting embodiment of collapsible mobile urine container 100 in a second state. As shown in FIGS. 2A and 2B, container body 102 may include body wall 104 and the top of body wall 104 may include exterior threading A. Cap 110 may include interior threading B. Threading A and threading B may be configured to interact with each other when cap 110 is in place on container body 102. For example, cap 110 may be threaded to container body 102 to prevent container body 102 from extending. During use, a user may unthread cap 110 from container body 102 to initiate extension of container body 102 for use. After use during a urination event or other fluid collection, a use may rethread cap 110 onto container body 102 to contain the liquid collected and container therein.

As further shown in FIG. 2A, container body 102 and body wall 104 may be made of a malleable polymeric material so that container body 102 may be extendible to a second state as demonstrated by section C. Similarly, flexible tube 106 may include tube wall 108 and tube wall 108 may be made of a malleable polymeric material so that flexible tube 106 may be extendible to a second state as demonstrated by section D. In a second state, as shown in FIGS. 2A and 2B and FIGS. 3A and 3B, collapsible mobile urine container 100 may extend, for example, to a height of six (6) inches to allow for use in a urination event. Collapsible mobile urine container 100 may be used during a urination event in a second state by placing the genitals above collapsible mobile urine container 100 and urinating into collapsible mobile urine container 100, or by inserting the penis into the top of the container body 102 and urinating into collapsible mobile urine container 100. Collapsible mobile urine container 100 may then be discarded by disposing container 100 in the proper receptacle. It is considered that, in some non-limiting embodiments, container body 102 may be removable from other components of container 100, and separately disposable. Other components may be reused.

Referring now to FIG. 4, FIG. 4 is a side view of a non-limiting embodiment of collapsible mobile urine container 100 in a third state. As shown in FIG. 4, collapsible mobile urine container 100 may be further extended to a third state. In a third state, flexible tube 106 is pulled out of container body 102 such that the second end of flexible tube 106 is pulled to the top of container body 102 and the first end of flexible tube 106 protrudes from container body 102. As shown in FIG. 4, the diameter of flexible tube wall 108 may be one and one-half (1 and ½) inches to allow for insertion of the penis. In a third state, the bottom of flexible tube 106 may be maintained inside the top of container body 102 by lip 116 so that flexible tube 106 may not be completely removed from container body 102. Collapsible mobile urine container 100 may be used during a urination event in a third state by placing the genitals above collapsible mobile urine container 100 and urinating into flexible tube 106, or by inserting the penis into the top of flexible tube 106 and urinating into collapsible mobile urine container 100. Collapsible mobile urine container 100 may then be discarded by disposing container 100 in the proper receptacle.

Figure 5:
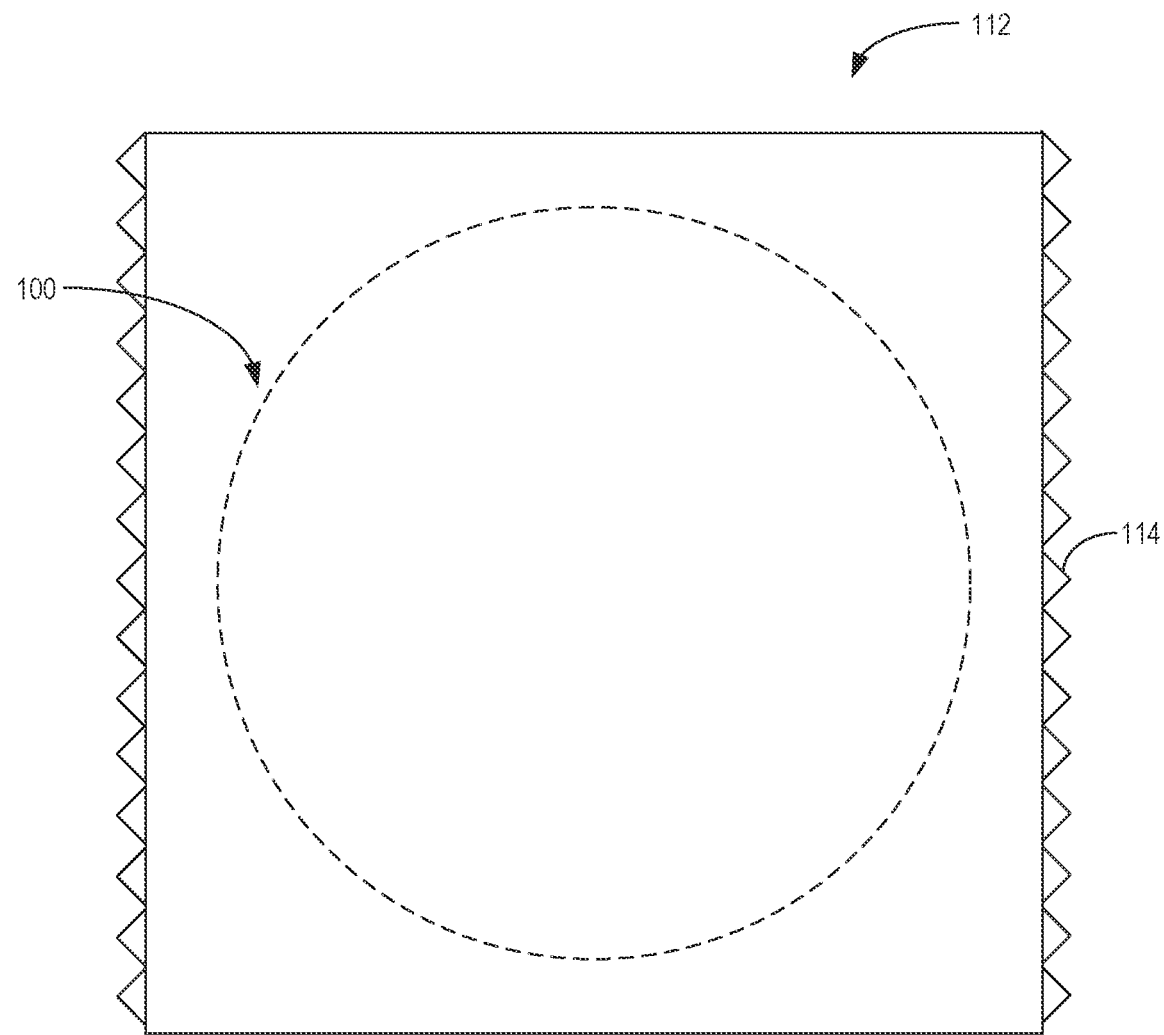
FIG. 5 is a plan view of a non-limiting embodiment of a packaging of a collapsible mobile urine container in accordance with the present disclosure.
Figure 6:
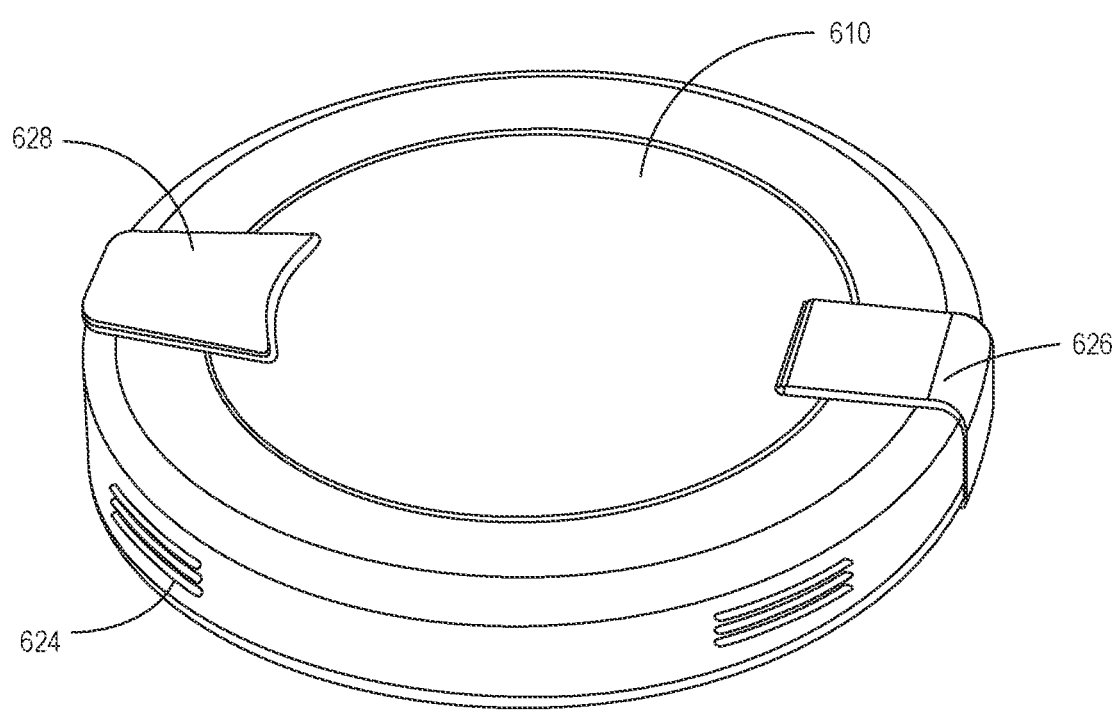
FIG. 6 is a perspective view of a non-limiting embodiment of a collapsible mobile urine container in accordance with the present disclosure.

Referring now to FIG. 5, FIG. 5 is a top view of a non-limiting embodiment of a packaging of a collapsible mobile urine container in accordance with the present disclosure. Packaging 112 may be made of sterile material to prevent bacteria or other infection causing substances from coming in contact with collapsible mobile urine container 100. As shown in FIG. 5, packaging 112 may be configured to enclose collapsible mobile urine container 100 in a first collapsed state. Packaging 112 may have a length of three (3) inches and a width of three (3) inches so as to be easily and discretely concealable in a clothes pocket, purse, or bag. As further shown in FIG. 5, packaging 112 may include serrated edges 114. Serrated edges 114 may be configured to allow tearing open of packing 112 to remove collapsible mobile urine container 100. After removal of collapsible mobile urine container 100, packaging 112 may be properly discarded.

Figure 7:
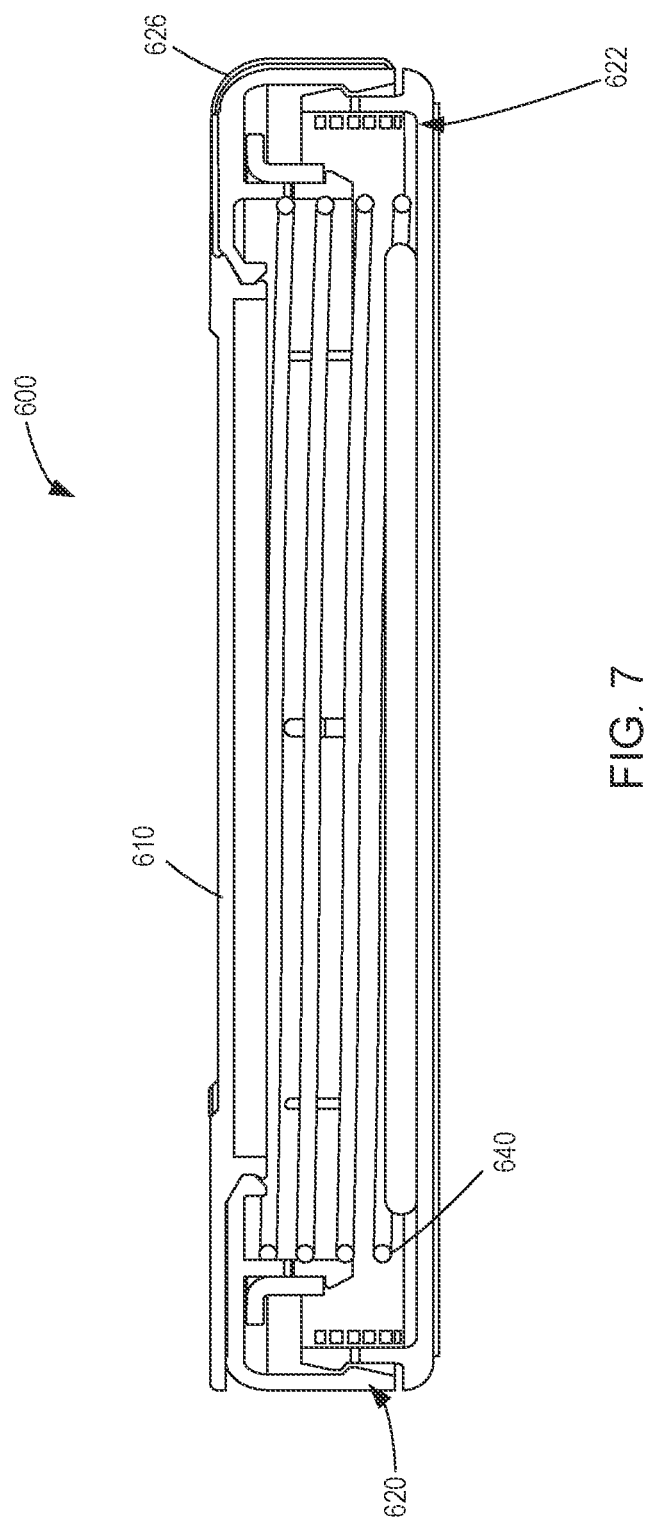
FIG. 7 is side sectional view of components of a non-limiting embodiment of a collapsible mobile urine container in accordance with the present disclosure.
Figure 8:
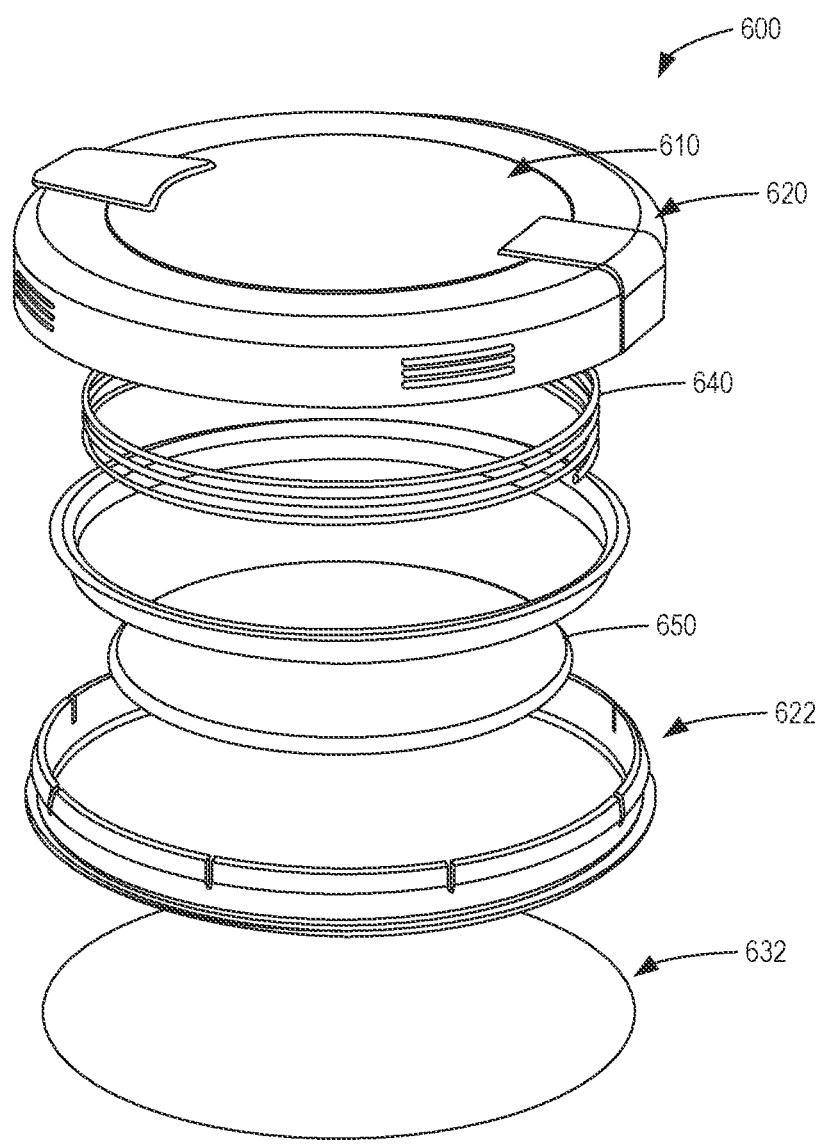
FIG. 8 is an exploded view of components of a non-limiting embodiment of a collapsible mobile urine container in accordance with the present disclosure.
Figure 9:
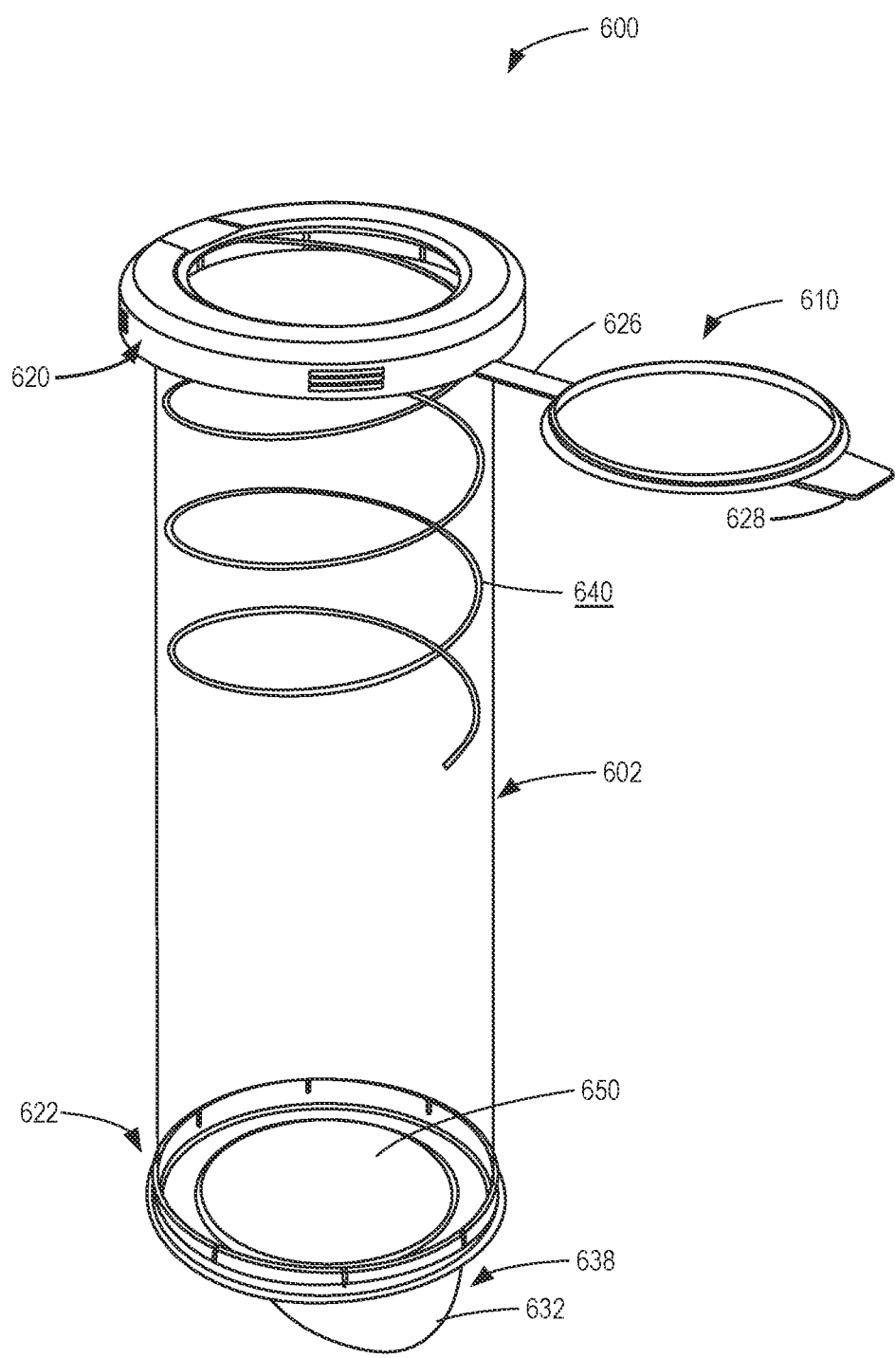
FIG. 9 is a perspective view of a non-limiting embodiment of a collapsible mobile urine container in a first state in accordance with the present disclosure.
Figure 10:
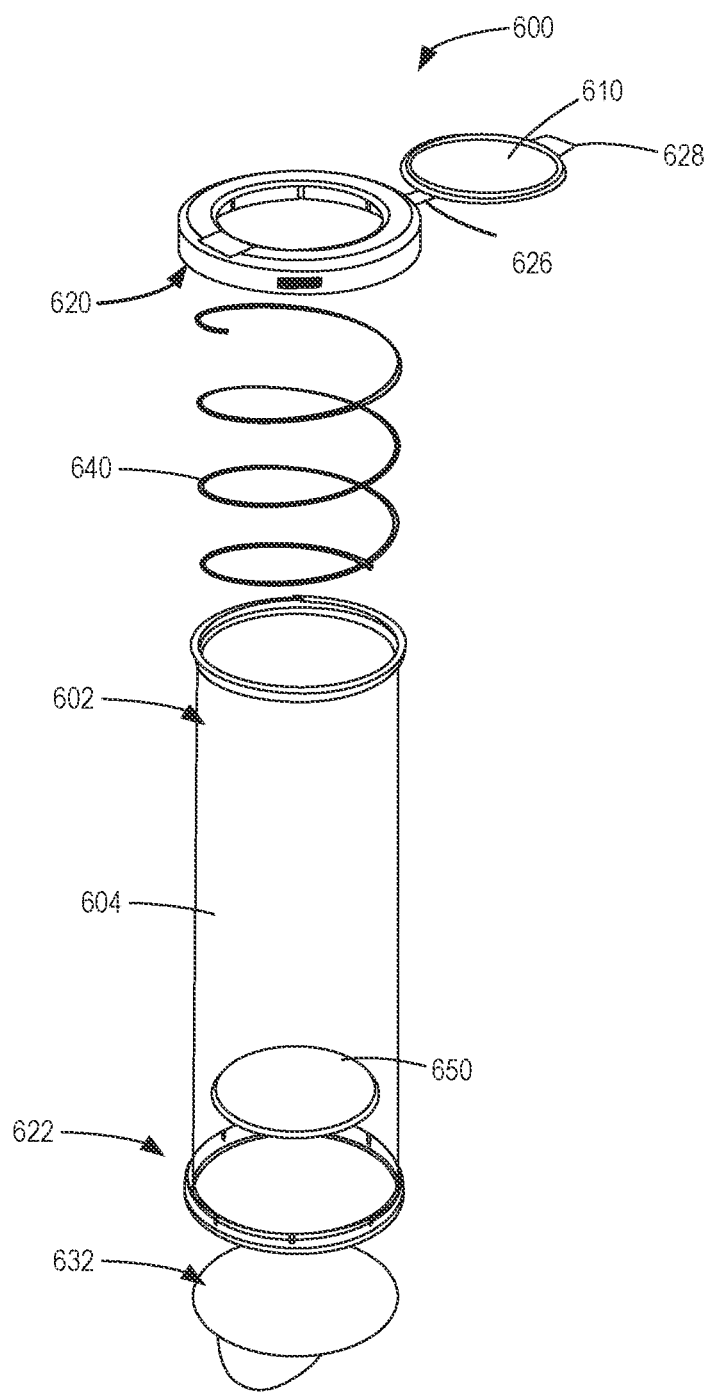
FIG. 10 is an exploded view of a non-limiting embodiment of a collapsible mobile urine container in accordance with the present disclosure.

Referring now to FIGS. 6-11C, FIGS. 6-11C are various views of a non-limiting embodiment of collapsible mobile urine container 600 in accordance with the present disclosure. Collapsible mobile urine container 600 may be the same as or similar to collapsible mobile urine container 100, where corresponding reference characters correspond to like parts. As shown in FIGS. 9 and 10, collapsible mobile urine container 600 may include container body 602, which may be made of malleable polymeric material and may have body wall 604, top 620, and bottom 622. Container body 602 may be configured to be collapsible such that container 600 can be easily and discretely concealed in a clothes pocket, purse, or bag. In some non-limiting embodiments, top 620 and bottom 622 to form a container shell. As shown in the illustrative non-limiting embodiments, body wall 604 may be a tube. In some non-limiting embodiments, body wall 604 may be a bag (e.g., as shown in FIGS. 12 and 14-16) or a tube. In some non-limiting embodiments, as shown in FIG. 7, top 620 and bottom 622 may attached to each other via friction fit or a clasp, or via another means such as threading. In this way, top 620 and bottom 620 may be held together to contain the bag or tube that comprises body wall 604 to maintain container 600 in a first collapsed state.

In some non-limiting embodiments, as shown in FIGS. 7-10 and 14-16, container body 602 may further comprise support member 640. In some non-limiting embodiments, support member 640 may be a coil such as a metal or wire coil. Alternatively, the support member may be comprised of a polymeric material, and may take a different shape. In some non-limiting embodiments, the coil may be a spring, and preferably, the coil may be a flat spring. Support member, such as the coil or spring shown in the illustrative embodiments, may provide structure to body wall 604. The structure provided by support member 640 may allow body wall 604 to hold its shape such that it prevents contact between the penis and container 600 where the penis is inserted into container 600 during use. Support member 640 may additionally bias top 620 away from bottom 622 to assist extension of body wall 602. Alternatively, support member 640 may bias top toward bottom 622 to assist in maintaining body wall 602 in a first collapsed state.

In some non-limiting embodiments, as shown in FIGS. 7 and 9, support member 640 may be coaxial with container body 602. As shown in FIG. 9, support member 640 may extend a distance from a first end of container body 602 (i.e., top 620) such that, in the second state, a height of support member 640 is less than a height of container body 602. In some non-limiting embodiments, support member 640 may extend a distance from a second end of container body 602 (i.e., bottom 622) such that, in the second state, a height of support member 640 is less than a height of container body 602. In some non-limiting embodiments, support member 640 may extend from a first end of container body 602 (i.e., top 620) to a second end of container body 602 (i.e., bottom 622).

In some non-limiting embodiments, as shown in FIGS. 6-11C, top 620 may comprise cap 610. In the illustrated embodiment, cap 610 may cover an opening through which liquids such as urine may be disposed into container 600.

During use, a user may remove cap 610 to access said opening. As shown in FIGS. 6-10, cap 610 may further comprise gripping members 624, hinge 626, and tab 628. Gripping members 624 and tab 628 may provide locations a user may hold to separate and remove cap 610 from top 620 of container 600. As shown in FIG. 9, hinge 626 may secure cap 610 to top 620 such that cap 610 does not impede use of container 600, improving sterility, but also such that cap 610 is not lost during a urination event, and may easily be replaced on top 620 to seal container 600 after a urination event. In some non-limiting embodiments, such as shown in FIGS. 8-10 and 11C, bottom 622 may comprise cover 632, which may be a structural component for sealing container body 602. In some non-limiting embodiments, cover 632 may be a sticker or label. In some non-limiting embodiments, cover 632 may further comprise tab 638. Tab 638 may provide a location a user may hold to extend container 600 from a first collapsed state to a second extended state.

In some non-limiting embodiments, as shown in FIGS. 8-10, container 600 may further include pad 650. In some non-limiting embodiments, pad 650 may be an absorbent powder pad. In some non-limiting embodiments, the absorbent powder pad may comprise a superabsorbent polymer (SAP). In some non-limiting embodiments, container 600 may instead include a water soluble bag with powder, or loose powder within container body 602. In some non-limiting embodiments, the powder may be sodium polyacrylate. Pad 650 may absorb and maintain the urine or other liquid within container 600, in some cases turning the liquid into a slush-like consistency. This effect may lessen the likelihood of spills, thus maintaining sterility prior to disposal.

Figure 11C:
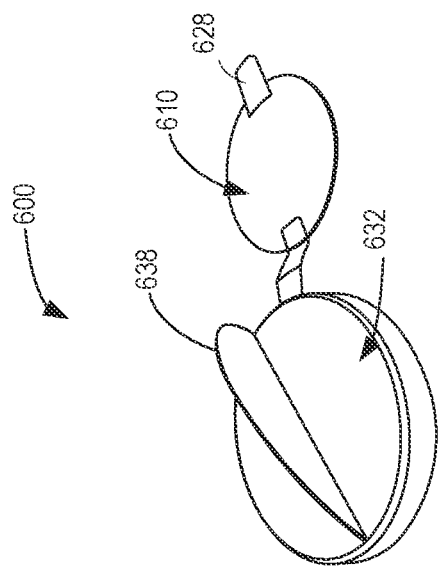
FIGS. 11A, 11B, and 11C are perspective views of a non-limiting embodiment of a collapsible mobile urine container in a collapsed state in accordance with the present disclosure.
Figure 11B:
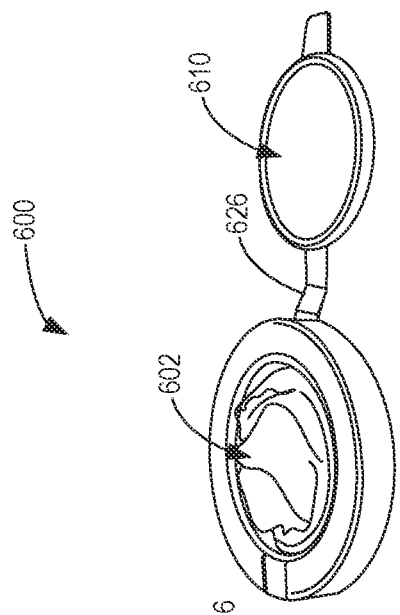
Figure 11A:
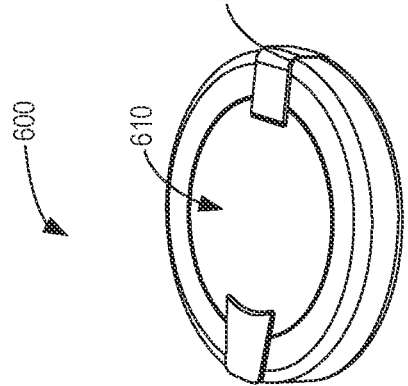

Referring now to FIGS. 11A-11C, FIGS. 11A-11C are top (FIGS. 11A-11B) and bottom (FIG. 11C) profile views of a non-limiting embodiment of a collapsible mobile urine container 600 in a collapsed state in accordance with the present disclosure. In the non-limiting embodiment shown in FIGS. 11A-11C, container 600 does not include gripping members 624. However, the illustrated non-limiting embodiment includes hinge 626 to secure cap 610 to container 600. Further, cap 610 includes tab 628 and cover 632 includes tab 638 to provide features for a user to grip or hold and pull, to both extend container 600 to the second, extended state, and to open cap 610. FIG. 11B shows container body 602 as a bag.

Figure 14:
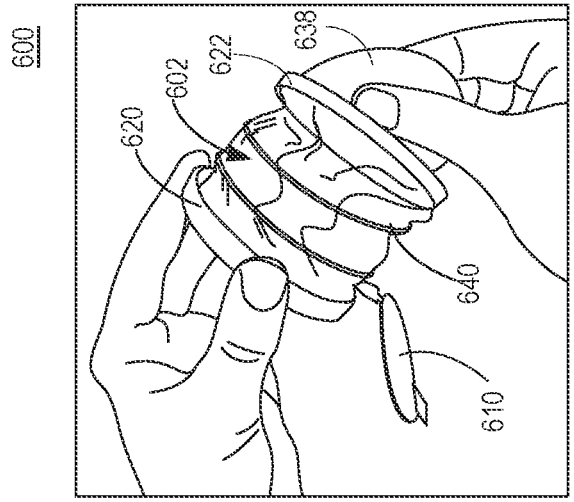
FIG. 14 is an illustrative view of a method step of using a non-limiting embodiment of a collapsible mobile urine container in accordance with the present disclosure.
Figure 13:
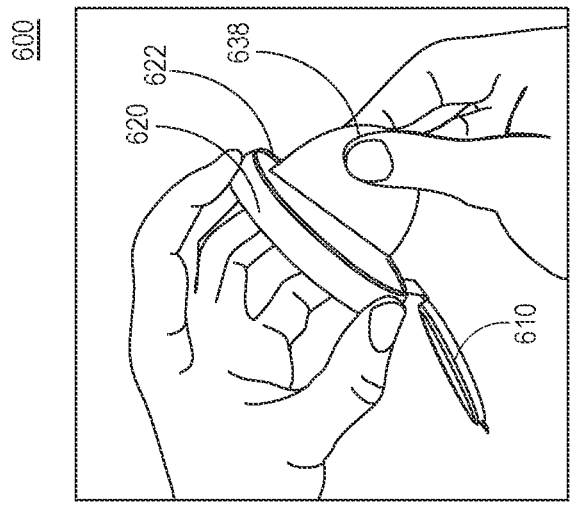
FIG. 13 is an illustrative view of a method step of using a non-limiting embodiment of a collapsible mobile urine container in accordance with the present disclosure.
Figure 12:
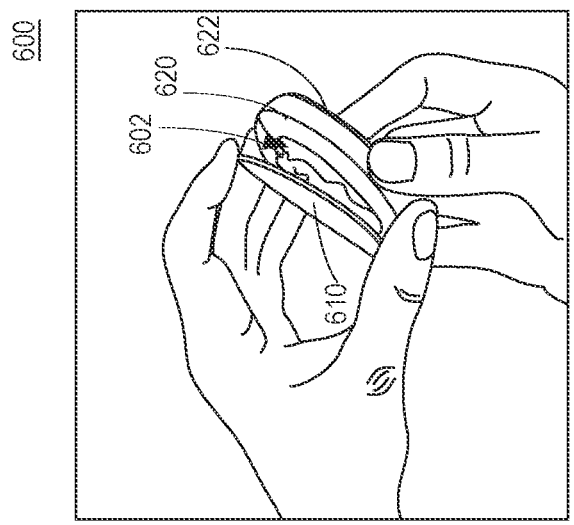
FIG. 12 is an illustrative view of a method step of using a non-limiting embodiment of a collapsible mobile urine container in accordance with the present disclosure.
Figure 16:
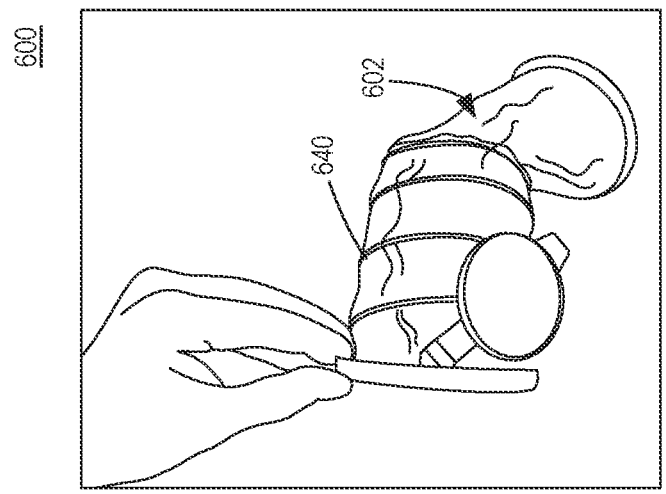
FIG. 16 is an illustrative view of a method step of using a non-limiting embodiment of a collapsible mobile urine container in accordance with the present disclosure.
Figure 15:
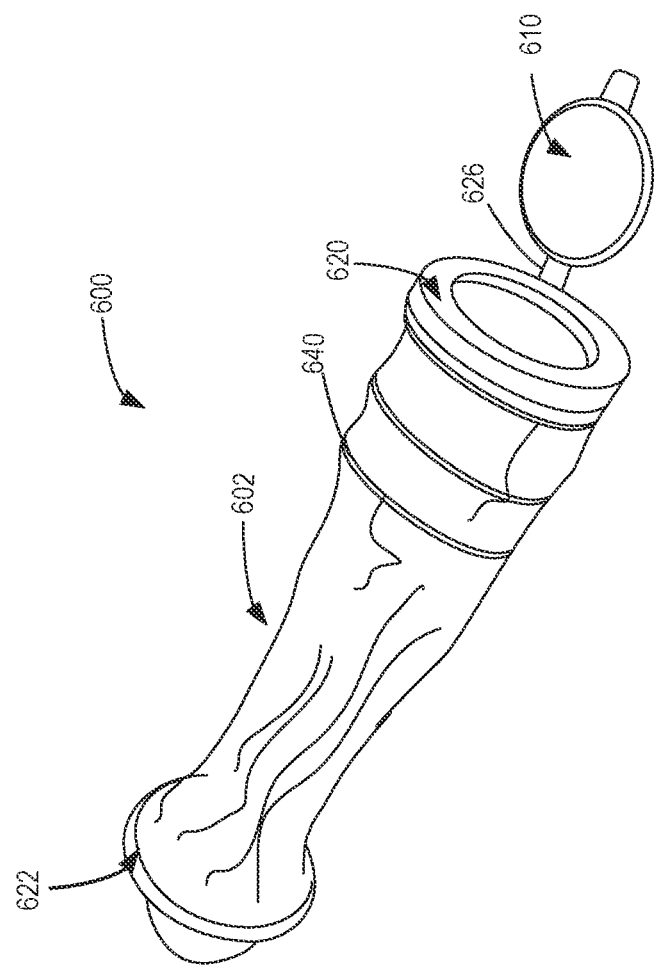
FIG. 15 is a perspective view of a non-limiting embodiment of a collapsible mobile urine container in an extended state during a method step of using a collapsible mobile urine container in accordance with the present disclosure.

Referring now to FIGS. 12-15, FIGS. 12-15 are views of method steps of using a non-limiting embodiment of a collapsible mobile urine container 600 in accordance with the present disclosure. A method of using a collapsible mobile urine container, such as container 100, 600, 700 (shown in FIGS. 17-25), may include providing a collapsible mobile urine container as disclosed herein. For example, in FIGS. 12-15, container 600 may be provided. The method may then include opening the container shell. In some non-limiting embodiments, as shown in FIG. 12, where the collapsible mobile urine container 600 includes a cap 610, opening the container shell may include opening cap 610 and removing it from top 620. Opening the container shell may further include gripping top 620 and bottom 622 to separate top 620 from bottom 622. A user may grip bottom 622 by holding tab 638 of cover 620, as shown in FIGS. 13-14. The method may then include extending the container body to the second state. An example of container 600 in the extended second state is shown in FIG. 15. The method may further include positioning container 600 and container body 602 relative to a user to collect urine, as shown in FIG. 16. Urine may then be collected in container 600 during a urination event. Once the urination event is completed, cap 610 may be repositioned on top 620 to contain the urine within container 600 to maintain sterility. Container 600 may then be discarded by disposing container 600 in the proper receptacle.

In some non-limiting embodiments, container 600 may be sized and configured to be collapsed to a minimal and concealable size in a first state, such that container 600 may be easily and discretely stored in a clothes pocket, purse, or bag. In the collapsed first state, container 600 may be collapsed to a height of less than three-quarters (¾) of an inch, and may preferably be one-half (½) of an inch, to allow for concealment of container 600. In some non-limiting embodiments, the diameter of the container body may be less than four (4) inches. For example the diameter of the container body may be three and one-half (3 and ½) inches, or preferably may be three and one-eighth (3 and ⅛) inches or three and three-sixteenths (3 and 3/16) inches. In some non-limiting embodiments, the diameter of an opening in top 620 for insertion of a penis or for reception of liquids may be between two (2) and three (3) inches, and preferably may be two and one-quarter (2 and ¼) inches. In a second state, collapsible mobile urine container 600 may extend, for example, such that container 600 extends to a height of at least five (5) inches, and preferably to a height of between six (6) and nine (9) inches. For example, container 600 may extend to a height of 6 and one-half (6 and ½) inches, or of eight (8) and three-quarters (8 and ¾) inches, to allow for use in a urination event. In some non-limiting embodiments, container 600 may be configured to retain a volume of up to thirty five (35) fluid ounces of liquid, and at least five (5) fluid ounces of liquid. Preferably, the container body may be configured to retain approximately twenty (20) fluid ounces of liquid, or approximately sixteen (16) fluid ounces of liquid. These enumerated dimensions allow for a concealable container body, but provide for retaining an adequate volume for a urination event, and allow for insertion of the penis into the container body. Said exemplary dimensions are not to be considered as limiting.

Referring now to FIGS. 17-25, FIGS. 17-25 are various perspective views of non-limiting embodiments of collapsible mobile urine container 700 in accordance with the present disclosure. Collapsible mobile urine container 700 may be the same as or similar to collapsible mobile urine container 100 and/or 600, where corresponding reference characters correspond to like parts. For example, container 700 may include a container body (similar to or the same as container body 602), made of malleable polymeric material, and having a body wall and support member 740. The body wall may comprise a bag or a tube.

The container body may be configured to be collapsible such that it is collapsed in a first state and extended in a second state. Accordingly, support member 740 may also be configured to be collapsible such that it is collapsed in a first state and extended in a second state. As shown in FIGS. 19-20 and 23-25, support member 740 may be a wire coil. Further, as also shown in FIGS. 19-20 and 23-25, the wire coil support member 740 may be a flat spring. The flat spring may provide structure and rigidity to the tube or bag making up the body wall. The structure provided by support member 740 may allow the body wall to hold its shape such that it prevents contact between the penis and container 700 where the penis is inserted into container 700 during use. Support member 740 may additionally bias the container body open to assist with extension of body wall 602. Alternatively, support member 740 may bias the container body closed to assist in maintaining the container body in a first collapsed state, especially while the container body is in shell 718.

Additionally, or alternatively, it is considered that the container body and or support member 740 may include an additional member for biasing the container body to a closed position. This additional body (not shown) may be a piece of tape, a snap, a button, tongue and groove, hook and loop, or another fastener of the like for biasing and maintaining the container body and support member 740 in a closed position.

Figure 18:
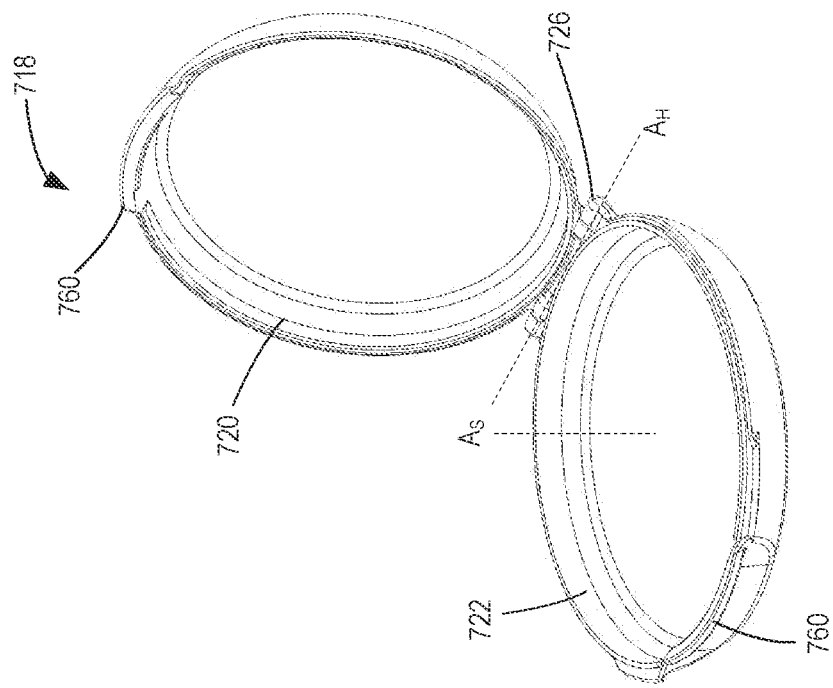
FIG. 18 is a perspective view of a container shell of a non-limiting embodiment of a collapsible mobile urine container in accordance with the present disclosure.
Figure 17:
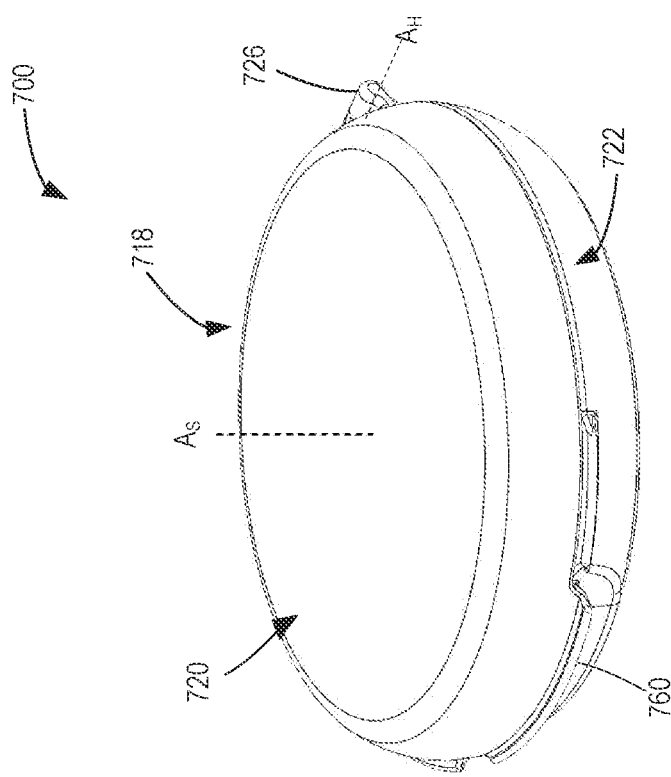
FIG. 17 is a perspective view of a non-limiting embodiment of a collapsible mobile urine container in accordance with the present disclosure.
Figure 20:
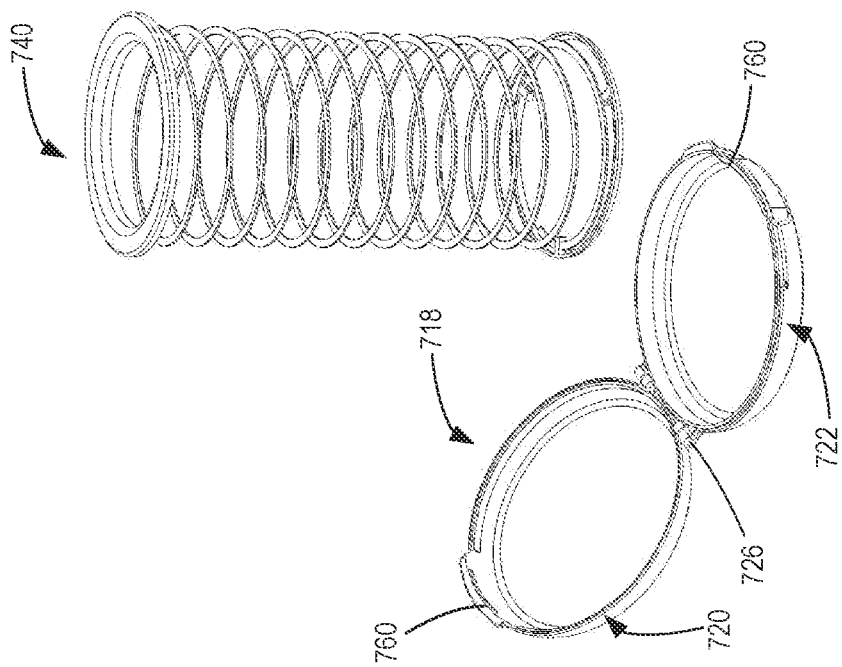
FIG. 20 is a perspective view of a non-limiting embodiment of a collapsible mobile urine container in an extended state in accordance with the present disclosure.
Figure 19:
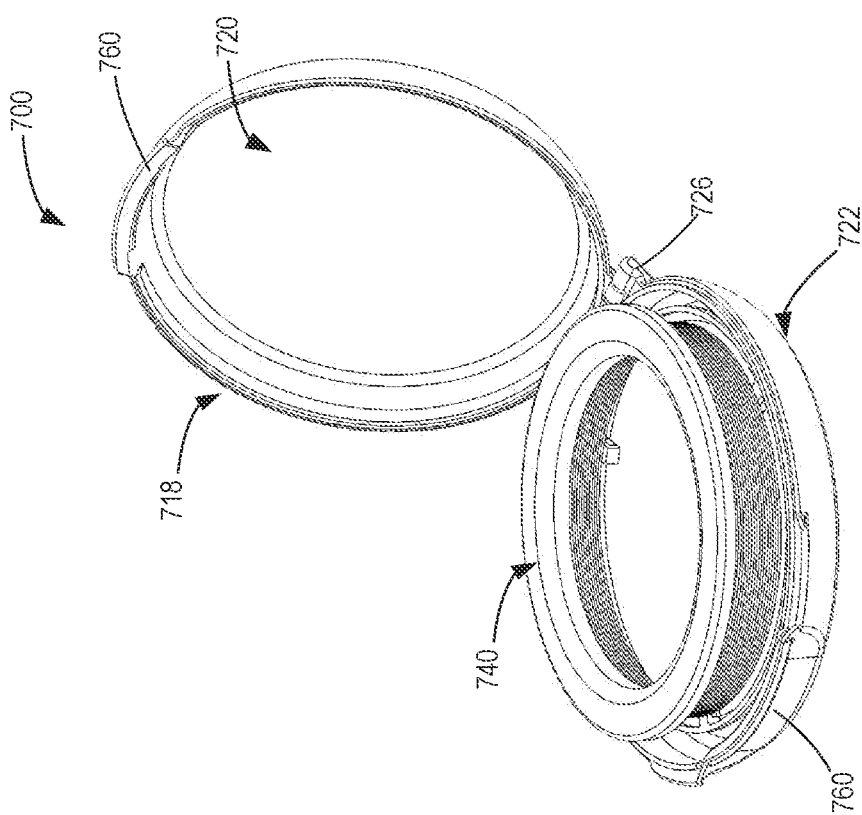
FIG. 19 is a perspective view of a non-limiting embodiment of a collapsible mobile urine container in a collapsed state in accordance with the present disclosure.
Figure 22:
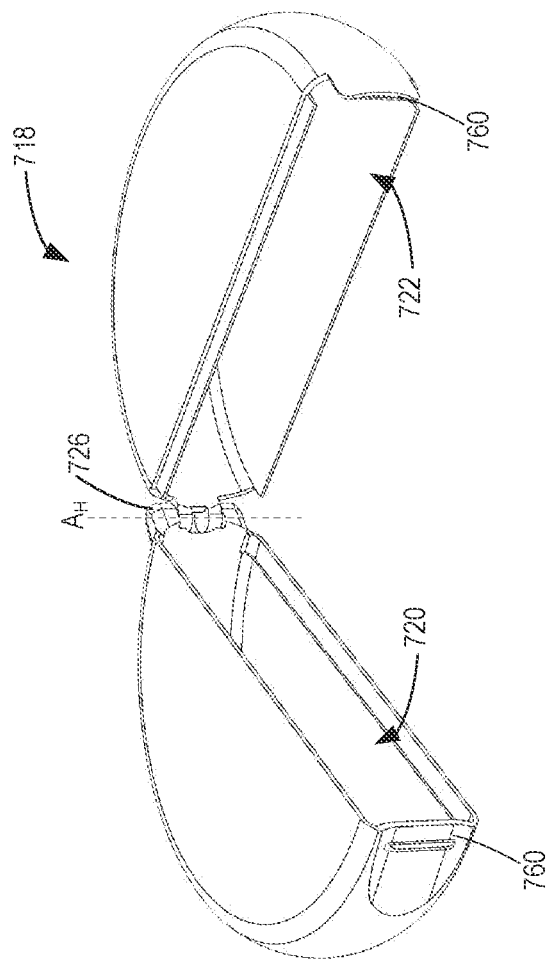
FIG. 22 is a perspective view of a non-limiting embodiment of a container shell of a collapsible mobile urine container in accordance with the present disclosure.
Figure 21:
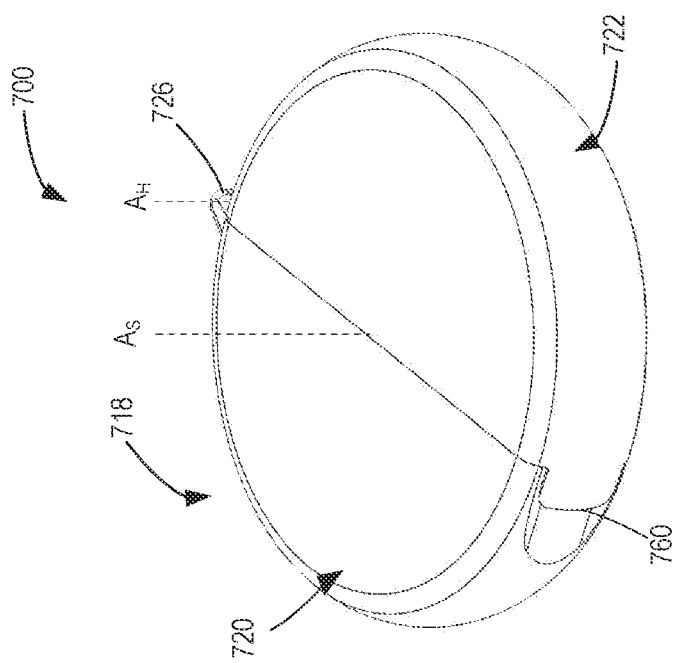
FIG. 21 is a perspective view of a non-limiting embodiment of a collapsible mobile urine container in accordance with the present disclosure.
Figure 24:
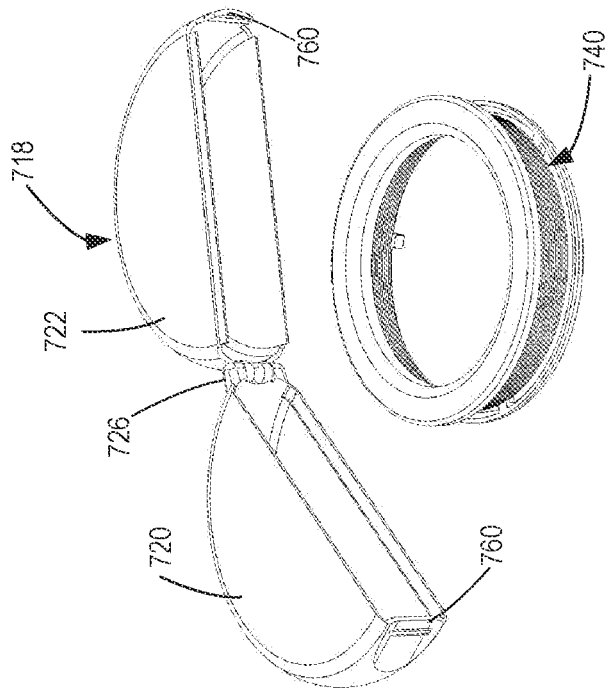
FIG. 24 is a perspective view of a non-limiting embodiment of a collapsible mobile urine container in a collapsed state in accordance with the present disclosure.
Figure 23:
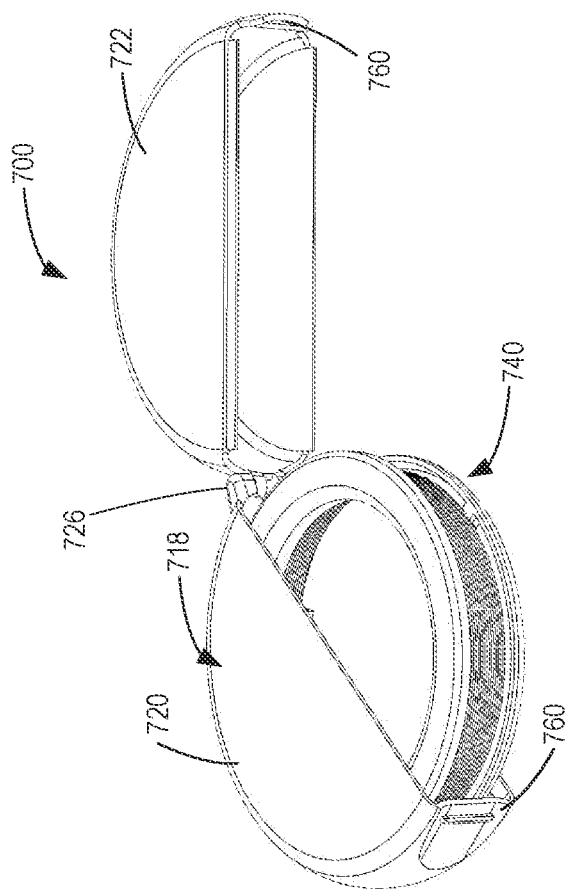
FIG. 23 is a perspective view of a non-limiting embodiment of a collapsible mobile urine container in a collapsed state in accordance with the present disclosure.
Figure 25:
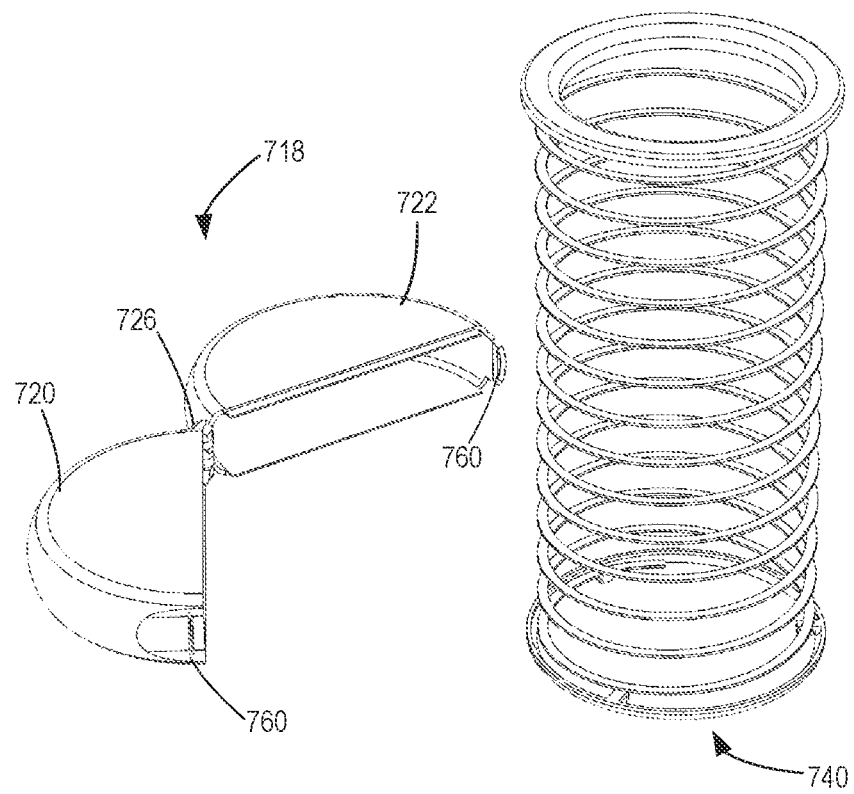
FIG. 25 is a perspective view of a non-limiting embodiment of a collapsible mobile urine container in an extended state in accordance with the present disclosure.

As shown in FIGS. 17-18, collapsible mobile urine container 700 may include container shell 718, and shell 718 may be comprised of top 720 and bottom 722. Container shell 718 may be configured to enclose the container body in the first state. Shell 718 may be configured as a clam-shell shape, such as shown in FIGS. 17-20. Accordingly, top 720 and bottom 722 may be hingedly connected such that an axis $A_H$ of hinge 726 connecting top 720 and bottom 722 may be perpendicular to central axis $A_S$ of container shell 718. Alternatively, shell 718 may be configured in a pie-sector or "Pac-Man®"-style shape, as shown in FIGS. 21-25. Accordingly, top 720 and bottom 722 may be hingedly connected such that an axis $A_H$ of hinge 726 connecting top 720 and bottom 722 may be parallel to central axis $A_S$ of container shell 718.

To maintain shell 718 in a closed position to contain the container body, shell 718 may include a clasp 760, or another similar means such as a piece of tape, a snap, a button, tongue and groove, hook and loop fastener, or the like, for holding shell 718 closed until use of container 700. As shown in FIGS. 17-25, each of top 720 and bottom 722 may be equipped with corresponding parts of clasp 760 that mate to hold shell 718 closed. Alternatively, in some non-limiting embodiments, top 720 and bottom 722 may be friction fit to maintain shell 718 in a closed position.

As shown in FIGS. 18, 20, 22, 24, and 25, the container body and support 740 may be removable from shell 718. This may allow a user to remove the container body from shell 718 to use the container body to collect urine during a urination event, and then to dispose of the container body, and reuse shell 718. Removal of the container body from shell 718 prior to use of container 700 during a urination event may allow the container to remain sterile. In such embodiments, the shell 718 of container 700 may be reused, such as by replacing the container body and support member 740 with another disposable container body.

In some non-limiting embodiments, container 700 may be sized and configured to be collapsed to a minimal and concealable size in a first state, such that container 700 may be easily and discretely stored in a clothes pocket, purse, or bag. In the collapsed first state, the container body may be collapsed to a height of less than three-quarters (¾) of an inch, and may preferably be one-half (½) of an inch, to allow for concealment of the container body within shell 718. Shell 718 may have a total height or thickness of less than one (1) inch, and preferably of seven-eighths (⅞) of an inch, when in a closed position. The diameter of shell 718 may be less than four (4) inches, and preferably may be approximately three and one-half (3 and ½) inches. In some non-limiting embodiments, the diameter of the container body may be less than three and one-half inches (3 and ½) inches, and preferably may be approximately three (3) inches. In a second state, collapsible mobile urine container 700 may extend, for example, such that the container body extends to a height of at least six (6) inches, and preferably of approximately eight (8) inches, to allow for use in a urination event. In some non-limiting embodiments, the container body may be configured to retain a volume of up to thirty-five (35) fluid ounces of liquid, and at least five (5) fluid ounces of liquid. Preferably, the container body may be configured to retain approximately twenty (20) fluid ounces of liquid, or approximately sixteen (16) fluid ounces of liquid. These enumerated dimensions allow for a concealable container body, but provide for retaining an adequate volume for a urination event, and allow for insertion of the penis into the container body. Said exemplary dimensions are not to be considered as limiting.

It is to be understood that, while the collapsible mobile urine container has been described and shown herein as being generally cylindrical, it is also contemplated that the container may take other shapes and forms such as a cube, cone, pyramid rectangular or triangular prism, or the like.

It is to be further understood, that while the container has been described so intended for the use of the collection of urine, it is also contemplated that other liquids or fluids can be collected in the collection container including, but not limited to, drinks, water, car oil, and blood.

While several examples of a collapsible mobile urine container, and methods of use are shown in the accompanying figures and described in detail hereinabove, other aspects will be apparent to, and readily made by, those skilled in the art without departing from the scope and spirit of the disclosure. Accordingly, the foregoing description is intended to be illustrative rather than restrictive. The invention described hereinabove is defined by the appended claims and all changes to the invention that fall within the meaning and range of equivalency of the claims are to be embraced within their scope.

What is claimed is:

1. A collapsible mobile urine container, comprising:
a container body comprised of malleable polymeric material and having a body wall, a top, and a bottom;
a cap covering an opening in the top;
a hinge securing the cap to the top such that the cap is held at a distance from the top when the cap is removed for use;
a tab extending from the cap; and
a clasp having a first clasp portion disposed on the top and a second clasp portion disposed on the bottom;
wherein the top and the bottom are fixed to the container body;
wherein the container body further comprises a support member and the support member is a coil,
wherein the coil is positioned inside of the body wall such that it is in communication with an open volume inside of the body wall,
wherein the coil extends a distance from the top such that a height of the coil is less than 75% of the height of the container when the container is in an extended state,
wherein the container body is configured to be collapsible, and
wherein the first clasp portion corresponds to the second clasp portion such that the clasp is configured to hold the top and the bottom together to maintain the container in a collapsed state.

2. The collapsible mobile urine container of claim 1, wherein the bottom comprises a cover and the cover comprises a tab.

3. The collapsible mobile urine container of claim 1, wherein the top further comprises gripping members.

4. The collapsible mobile urine container of claim 1, wherein the container body is configured to be collapsible such that it is compact or small enough to fit in a clothes pocket.

5. The collapsible mobile urine container of claim 1, wherein the body wall is a bag or a tube.

6. The collapsible mobile urine container of claim 1, wherein the container has a total thickness of less than one inch in the collapsed state,
   wherein the container has a total height of between six and nine inches in the extended state, and
   wherein the container has an outer diameter of less than four inches.

7. A collapsible mobile urine container, comprising:
   a container body comprised of malleable polymeric material and having a body wall and a support member positioned inside the body wall such that the support member is in open communication with an open volume inside of the body wall; and
   a container shell having a top and a bottom,
   wherein the container body is configured to be collapsible such that it is collapsed in a first state and extended in a second state,
   wherein the container shell is configured to enclose the container body in the first state,
   wherein the support member extends a distance from a top end of the container body such that a height of the support is less than 75% of the height of the container body when the container body is in the second state,
   wherein the container shell comprises a clasp having a first clasp portion disposed on the top and a second clasp portion disposed on the bottom,
   wherein the first clasp portion corresponds to the second clasp portion such that the clasp is configured to hold the top and the bottom together to maintain the container body in a collapsed state inside of the container shell,
   wherein the top and the bottom are hingedly connected such that an axis of a hinge connecting the top and the bottom is parallel to a central axis of the container shell, and
   wherein the entire container body is removable from the container shell.

8. The collapsible mobile urine container of claim 7, wherein the body wall comprises a bag or a tube.

9. The collapsible mobile urine container of claim 7, wherein the support member is a wire coil.

10. The collapsible mobile urine container of claim 9, wherein the wire coil is a flat spring, and
    wherein the flat spring is coaxial with the container body.

11. The collapsible mobile urine container of claim 7, wherein the container body has a total thickness of less than one inch in a collapsed first state,
    wherein the container shell has a total thickness of less than one inch in a closed position,
    wherein the container body has a total height of between six and nine inches in an extended second state, and
    wherein the container body has an outer diameter of less than four inches.

12. A method of using a collapsible mobile urine container, the method comprising:
    providing a collapsible mobile urine container comprising:
       a container body comprised of malleable polymeric material and having a body wall and a support member positioned inside the body wall such that the support member is in open communication with an open volume inside of the body wall; and
       a container shell having a top and a bottom,
       wherein the container body is configured to be collapsible such that it is collapsed in a first state and extended in a second state,
       wherein the container shell encloses the container body in the first state,
       wherein the support member extends a distance from a top end of the container body such that a height of the support is less than 75% of the height of the container body when the container body is in the second state,
       wherein the container shell comprises a clasp having a first clasp portion disposed on the top and a second clasp portion disposed on the bottom,
       wherein the first clasp portion corresponds to the second clasp portion such that the clasp is configured to hold the top and the bottom together to maintain the container body in a collapsed state inside of the container shell,
       wherein the top and the bottom are hingedly connected such that an axis of a hinge connecting the top and the bottom is parallel to a central axis of the container shell, and
       wherein the entire container body is removable from the container shell, opening the container shell;
    extending the container body to the second state;
    positioning the container body relative to a user to collect urine; and
    collecting urine during a urination event.

13. The collapsible mobile urine container of claim 1, wherein the container further comprises:
    an absorbent powder configured to absorb and maintain urine within the container.

14. The collapsible mobile urine container of claim 1, wherein the container further comprises:
    an absorbent powder pad comprising a superabsorbent polymer configured to absorb and maintain urine within the container.

* * * * *